United States Patent [19]

Czabaffy et al.

[11] Patent Number: 4,632,549
[45] Date of Patent: Dec. 30, 1986

[54] METHOD FOR MEASURING SPECTRA OF MATERIALS

[75] Inventors: András Czabaffy; Károly Kaffka; Loránd Horváth; Béla Nádai, all of Budapest, Hungary

[73] Assignee: Kozponti Elelmiszeripari Kutato Intezet, Hungary

[21] Appl. No.: 485,049

[22] Filed: Apr. 14, 1983

[30] Foreign Application Priority Data

Apr. 14, 1982 [HU] Hungary .............................. 1139/82

[51] Int. Cl.[4] .............................................. G01J 3/42
[52] U.S. Cl. .................................... 356/300; 356/323; 356/326
[58] Field of Search ............... 356/319, 323, 325, 300, 356/326, 328; 364/498

[56] References Cited

U.S. PATENT DOCUMENTS

| | | |
|---|---|---|
| 3,935,463 | 1/1976 | Jacobsen . |
| 4,035,083 | 7/1977 | Woodriff et al. . |
| 4,105,333 | 8/1978 | Kaule et al. . |
| 4,299,485 | 11/1981 | Barlow et al. .................. 356/323 X |
| 4,357,673 | 11/1982 | Willis et al. ..................... 356/323 X |
| 4,488,811 | 12/1984 | Fukuma .............................. 356/319 |

Primary Examiner—F. L. Evans
Attorney, Agent, or Firm—Young & Thompson

[57] ABSTRACT

The invention provides on a method for measuring the spectrum of a material, wherein a sample (10) of the material to be tested is irradiated with a radiation of required wavelengths and the spectrum signals produced by an intensity measuring unit (34) as a result of the radiation reflected or transmitted by the sample (10) are measured. According to the present invention, a zero level signal produced by the intensity measuring unit (34) in an unradiated condition is measured and the measured zero level value is stored, then one or more spectrum signal measurements are performed at at least one wavelength and the measured one or more spectrum values are stored, then the zero level signal produced by the intensity measuring unit (34) is measured again in an unradiated condition and its value is stored, then preferably those one or more spectrum signal measurements at at least one wavelength prescribed and the storage of the measured values as well as the zero level signal measurement and the storage of the measured value are repeated as many times as required, and finally the stored spectrum values are modified by correction values generated on the basis of the stored zero level values.

13 Claims, 7 Drawing Figures

METHOD FOR MEASURING SPECTRA OF MATERIALS

The subject matter of the present invention is a method and an apparatus for measuring spectra of materials.

BACKGROUND ART

Solid state photoresistors or photodiodes are frequently applied in photometers and spectrophotometers as sensing elements to detect radiation. These sensors are connected to a suitable measuring circuit so that the output voltage of the resulting intensity measuring unit should be proportional to the radiation to be measured. However, the dark resistance of the photoresistors, i.e. the measurable resistance of unradiated photresistors is not of infinite but of finite value depending also on temperature. Likewise the dark current of photodiodes is not zero either, but of finite value depending also on temperature. Dark resistance and dark current, respectively, is effected also by nuclear radiation ($\alpha$, $\beta$, $\gamma$) acting on the sensor; furthermore the value of these parameters is subjected to permanent changes during the useful lifetime of these devices. Consequently the output voltage of the aforementioned intensity measuring unit is not zero even if the sensor capable of detecting radiation is not subjected to radiation at all, but it has a small finite value slightly changing in time. In case of measuring a spectrum the useful signal is superimposed onto this slowly changing zero level signal. The voltage detected at the output of the intensity measuring unit therefore includes the momentary value of the zero level voltage added to the voltage characterizing the intensity of the radiation to be measured.

Since the intensity of the measured radiation is characterized only by the latter, an effort is made to establish the value of the zero level voltage and to subtract it—automatically, if possible—from the output voltage; thereby the resulting differential voltage will only be characteristic to the intensity of the radiation to be measured. A wide-spread solution to this problem is to intermittently cut the beam path of the spectrometer and then to measure the value of the zero level voltage on the output of the intensity measuring unit; this value is stored by analog means and is subtracted from the output voltage of the amplifier during the measuring period following the opening of the beam path. Another solution is also known whereby a suitable voltage or current is applied to the input of the amplifier connected to the sensor while the diaphragm cuts off the beam path so that the output voltage should be set to zero and then, during the subsequent measuring period this voltage or current stored by analogue means remains applied to the input; thereby the output voltage will characterize only the intensity of the measured radiation acting upon the sensor.

These methods apparently eliminate the error resulting from the variations of zero level signal. Acutally the error partly remains, and if the conditions are unfavourable an undesirable additional error can even occur. The former error can be attributed to theoretical, the latter to practical reasons. The residual error attributed to theoretical reasons is the result of the fact that the output voltage compensated at the beginning of the measuring period would only remain zero during the measuring period if the dark signal of the sensing element did not change meanwhile. Practically, however, the dark signal and thereby the zero level signal is even subjected to variations in the interval of the measuring period and this variation results in a measuring error. The undesirable additional error is the result of the analog method of storing the voltage necessary to compensate the output, namely a capacitor charged to the required voltage to store it during the next measuring period. This storage can however be of limited accuracy, since some of the charge will be lost partly as a result of the conductivity of the capacitor and partly as a result of the finite resistance of the circuits connected. Consequently, the output voltage accurately zeroed at the beginning of the measuring period would differ from zero at the end of the measuring period even if the dark signal of the sensing element did not change meanwhile.

There is only one condition for the zero output voltage not to change during the measuring period: when the errors resulting from the loss of charge in the capacitor and the variations of the zero level are equal and of opposite polarity. This can only occur occasionally and within a relatively short interval; it can not be relied on. Therefore with the equipment known so far the accuracy of the measurement in the course of the measuring period continuously deteriorates, since the spectrum signal characteristic of the intensity of the radiation to be measured is superimposed onto a nearly saw-tooth shaped time-dependent zero level signal.

DISCLOSURE OF INVENTION

Therefore, it is an object of the present invention to increase the measuring accuracy of the method and apparatus described above. The method and apparatus provided by the present invention is based on the following basic ideas.

(a) The slow change in the dark signal of the sensor detecting the radiation can be attributed mostly to thermal reasons and the relatively short-time periods of slow thermal variations can be well approximated by linear functions.

(b) The initial period of the loss of charge in the storage capacitor of the level compensating circuit can also be well approximated by a linear function.

(c) Knowing two different values of the zero level signal measured successively in a time interval relatively short compared to the thermal time constant, the value of the zero level signal can be linearly well interpolated for any moment within said interval; and if a set of measurements is provided giving different zero level signals plotted against time, where the time interval between the individual measurements is relatively short compared to the thermal time constant, even more accurate values can be attained for intermediate moments by applying a higher order approximation for the interpolation.

Therefore the invention on the one hand provides a method for measuring the spectrum of a material, comprising the steps of irradiating a sample of the material to be tested with a radiation of required wavelengths and measuring spectrum signals produced by an intensity measuring unit as a result of the radiation reflected or transmitted by the sample. This method is characterized by first measuring a zero level signal produced by the intensity measuring unit in an unradiated condition and storing the measured zero level value, then measuring one or more spectrum signals at at least one wavelength and storing the one or more spectrum signal values, then measuring again the zero level signal produced by the intensity measuring unit in an unradiated condition and storing the measured value, preferably said one or more spectrum signal measurements at at least one predetermined wavelength and said storage of the measured values as well as said zero level signal measurement and said storage of the measured value are repeated as many times as required, and finally modifying the stored spectrum values by correction values generated on the basis of the stored zero level values.

The present invention also relates to a method for measuring the spectrum of a material, comprising the steps of irradiating a sample of the material to be tested with a radiation of required wavelengths and measuring spectrum signals produced by an intensity measuring unit as a result of the radiation reflected or transmitted by the sample, wherein the intensity measuring unit is set to zero in an unradiated condition. This method is characterized by measuring one or more spectrum signals at at least one wavelength following the zeroing of the intensity measuring unit and storing the one or more measured spectrum values, then measuring the zero level signal produced by the intensity measuring unit in an unradiated condition and storing the measured zero level value, then preferably said one or more spectrum signal measurements at at least one predetermined wavelength and said storage of the measured values as well as said zero level signal measurement and said storage of the measured value are repeated as many times as required, and finally modifying the stored spectrum values by correction values generated on the basis of the stored zero level value(s).

The method according to the invention makes it possible to attain a higher accuracy of measurement than by the methods known heretofore, since based on the zeroing and/or measurement of the zero level preceding the period of spectrum measurement and the measurement of the zero level succeeding the period of spectrum measurement, each spectrum value measured during the period of measurement is modified by a correction value corresponding to the exact time of the measurement, which correction value approximates very well the time-dependent variation of the zero level within the period of the measurement. The correction values can preferably be generated by linear interpolation. Inasmuch the value of the zero level signal is always measured between several periods of spectrum measurements, the accuracy can further be increased by applying a higher order approximation.

It is a very advantageous implementation of the method provided by the present invention where the measurement of the zero level signal and the storage of the zero level value are performed by several successive measurements of the signal produced by the intensity measuring unit being in an unradiated condition and storing the values measured. In this case the zero level values derived from the averaging of the values of succesive measurements are employed to generate the correction values, so the effect of interferences or noise occurring also in the course of the zero level measurements is considerably reduced. Likewise it is also preferred to determine each spectrum value by averaging the results of several succesive measurements.

The present invention on the other hand provides an apparatus for measuring the spectrum of a material, comprising a controllable monochromator emitting radiation of a required wavelength onto a sample of the material to be tested, an intensity measuring unit provided with a sensor sensitive to the radiation reflected or transmitted by the sample, a data processing unit connected to the intensity measuring unit via an analog-to-digital converter, and a control unit controlling the analog-to-digital converter synchronously with the monochromator while irradiating the sample with radiation of the required wavelength. This apparatus is characterized according to the present invention in that said control unit comprises means to provide at least one start signal to a control input of the analog-to-digital converter prior to and/or after the period of irradiating the sample with radiation of the required wavelength.

In a preferred embodiment of the apparatus, the control unit comprises a rotatable member attached to a shaft controlling the wavelength of the radiation emitted by the monochromator, an auxiliary light source and an auxiliary detector sensitive to the light of the auxiliary light source, said rotatable member being positioned between the monochromator and the sample as well as between the auxiliary light source and the auxiliary detector, said rotatable member being provided with a radiation-transparent section formed as a diaphragm in the path of the radiation beam emitted by the monochromator and at least one first opening transparent to light and formed as a diaphragm in the path of the light beam of the auxiliary light source and positioned rotationally preceding and/or succeeding said radiation-transparent section, and an output of the auxiliary detector being connected to the control input of the analog-to-digital converter. With this embodiment the rotatable member is advantageously provided with at least one transparent second opening rotationally aligned with said radiation-transparent section and formed as a diaphragm in the path of the light beam of the auxiliary light source. In this case, timing of the zero level signal measurements as well as the spectrum signal measurements is controlled by the rotatable member, preferably shaped as a disc, a cup or a drum. The rotatable member can also be applied to control the zeroing operation, for this purpose the apparatus is provided with a further auxiliary light source and a further auxiliary detector sensitive to the light of said further auxiliary light source, said rotatable member being provided with a transparent third opening formed as a diaphragm in the path of the light beam of the further auxiliary light source and positioned rotationally preceding said radiation-transparent section, and an output of the further auxiliary detector is connected to a zeroing input of the intensity measuring unit.

In another embodiment of the invention the output of the auxiliary detector is connected to the control input of the analog-to-digital converter via an electronic timing circuit. In this case only the timing circuit is started by the corresponding opening provided on said rotatable member, and the timing of the zero level measurements as well as the timing of the spectrum measurements—preferably the zeroing, too—are performed by the electronic timing circuit, e.g. by a microprocessor.

In another preferred embodiment of the apparatus according to the present invention the data processing unit and the control unit are realized by a microprocessor having first and second control outputs, the first control output being connected to the control input of the analog-to-digital converter and the second control output being connected to a device controlling the monochromator. A third control output of the microprocessor may expediently control the zeroing of the intensity measuring unit. The control of the monochromator can preferably be realized by applying a stepper motor as a control device for the monochromator, the stepper motor being connected to said second control output of the microprocessor via a motor control unit. Furthermore the apparatus may be provided with an electromagnetically operated diaphragm in the path of the radiation beam emitted by the monochromator and a driver unit for the diaphragm, said driver unit being connected to a fourth control output of the microprocessor. Few mechanical parts, little space requirement and a high reliability are the advantages of this emobdiment.

BRIEF DESCRIPTION OF THE DRAWINGS

The invention is described in the following on the basis of preferred embodiments illustrated in the accompanying drawings, in which.

MODES FOR CARRYING OUT THE INVENTION

Figure 1:
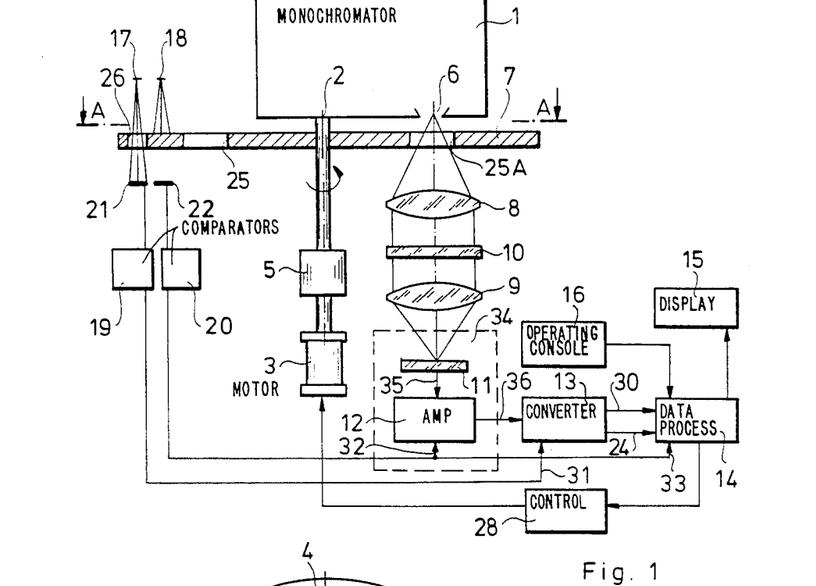
FIG. 1 is a block diagram of an embodiment of the apparatus according to the invention.
Figure 2:
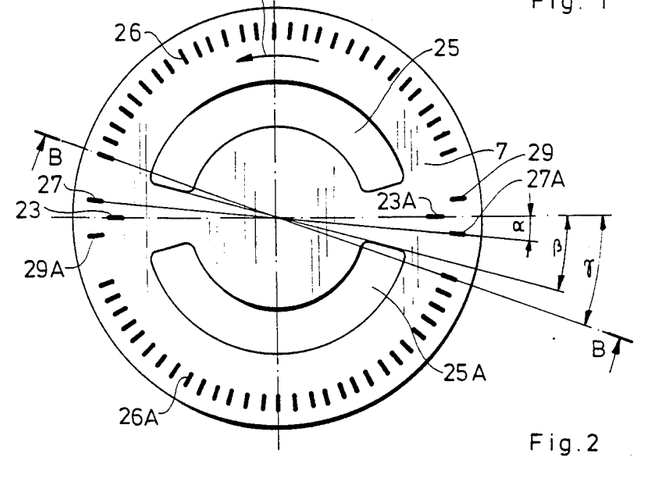
FIG. 2 is a top view of the disc-shaped rotatable member of the apparatus illustrated in FIG. 1.

The apparatus illustrated in FIG. 1 comprises a disc-shaped rotatable member 7, the top view of which taken along the section line A—A of FIG. 1 is shown in FIG. 2. In FIG. 1 the rotatable member 7 is illustrated in a position corresponding to section line B—B of FIG. 2. The radiation of the required wavelength is produced by a monochromator 1, the beam of which is emitted through a slit 6. The wavelength of the emitted beam depends on the angular position of a control shaft 2 of the monochromator 1. The shaft 2 is driven by a motor 3—in this case via a unit 5 changing rotational speed—and the motor 3 is connected to an output of a motor control unit 28. The beam of radiation emitted through the slit 6, passing through a radiation-transparent secton 25A of the disc-shaped rotatable element 7 which is in the position illustrated in FIG. 1 and through a lens 8, is applied to a sample 10 to be measured, then the beam transmitted by the sample 10 passes through a lens 9 and reaches the input of a sensor 11 sensitive to the radiation. The sensor 11 must be selected according to the wavelength of the radiation, it may be for example a photodiode or a photoresistor providing an analog electric signal at its output proportional to the intensity of the beam of radiation applied to its input. This electric signal is applied to the input of a zeroable amplifier 12 providing an amplified analog signal at its output 36. As a result of a control signal applied to the zeroing input 32 of the amplifier 12, the zero level will be restored at the output 36 as it will be described later in detail referring to FIG. 4. The sensor 11 and the amplifier 12 together constitute an intensity measuring unit 34 providing at its output 36 an analog electric signal, i.e. voltage, proportional to the intensity of the beam of radiation applied to its input sensitive to the radiation, and which is zeroed under the effect of a signal applied to its zeroing input 32.

The output 36 is connected to the analog input of an analog-to-digital converter 13. The analog-to-digital converter 13 converts the analog signal existing at its input into a digital signal at the moment when a signal is applied to its control input 31. The digital signal generated by the analog-to-digital converter 13 is transferred via parallel line 30 into a data processing unit 14 strobed by a start signal via control line 24 to read the digital signal. A display unit 15 is connected to the data processing unit 14, and the operator can communicate with the data processing unit 14 via an operating console 16. The motor control unit 28 is also controlled by the data processing unit 14.

The apparatus comprises furthermore an auxiliary light source 17 and an auxiliary detector 21 placed oppositely, and the latter is connected to a comparator 19, the output of which is connected to the control input 31 of the analog-to-digital converter 13. A further auxiliary light source 18 and a further auxiliary detector 22 are also placed oppositely, and the output of the latter is connected, via a comparator 20, to the zeroing input 32 of the amplifier 12 and to the input 33 initiating a data input operation of the data processing unit 14.

The apparatus is controlled by means of the openings or slots provided on the disc-shaped rotatable member 7. As can be seen in FIG. 2, an opening 27, openings 26 and an opening 29 are successively formed in one half of the rotatable member 7 opposite the auxiliary light source 17, and similar openings 27A, 26A and 29A are formed centrally symmetrical with respect to the aforementioned openings in the other half of the rotatable member 7, too. Openings 23 and 23A are provided opposite the auxiliary light source 18. Opposite the exit slit 6 of the monochromator 1 there are sections 25 and 25A transparent to the radiation, sections non-transparent to the radiation being provided between the sections 25 and 25A.

The apparatus illustrated in FIGS. 1 and 2 is applied to perform measurements as described in the following. Having switched on the apparatus and after the insertion of the sample 10, the operator starts the measuring period via the operating console 16 by giving a start signal to the data processing unit 14 e.g. to a microprocessor, thereby the data processing unit 14 powers the motor control unit 28. Thereupon the motor 3 starts to rotate the rotatable member 7. As a result of the light pulse transmitted through the opening 23 on the one hand the intensity measuring unit 34 will be set to zero, since the rotatable member 7 prevents the radiation emitted from the monochromator 1 to from reaching the sample 10 and so the input of the sensor 11, on the other hand the data processing unit 14 will be enabled to receive digital output signals of the analog-to-digital converter 13 as a result of the control signal applied to its input 33. As soon as the rotatable member 7 has been rotated through an angle α in the direction indicated by the arrow 4, as a result of the light pulse transmitted through the opening 27 the comparator 19 provides a signal to the control input 31 of the analog-to-digital converter 13 which measures the zero level signal existing on the output 36 as the radiation is still prevented to reach the input of the sensor 11 by the rotatable member 7. The value of the zero level signal will be stored in the main memory of the data processing unit 14. As soon as the rotatable member 7 has been rotatated through an angle β, the radiation emitted from the slit 6 of the monochromator 1 and passing through the section 25A transparent to the said radiation reaches the sample 10 and then the sensor 11. When the rotatable member 7 is rotated through an angle γ, as a result of the light pulse transmitted through the first one of the openings 26 the analog-to-digital converter 13 performs a spectrum signal measurement at a wavelength defined by the angular position of the shaft 2, and the value measured will be stored in the data processing unit 14. While the rotatable member 7 is further rotating, subsequent measurements will be performed corresponding to the openings 26 and the measured values will be stored. Thereafter the path of the beam of radiation emitted from the slit 6 will be cut again by the rotatable member 7 and then a zero level signal measurement and storage of its value will occur again as a result of the light pulse transmitted through the opening 29. As soon as the rotatable member 7 completes a half turn, a new sequence of measurement is started with a zero setting effected by a light pulse transmitted through the opening 23A. In this embodiment of the invention each of the openings 26 and 26A corresponds to a certain wave length value, and the total spectrum measurement is performed during a half turn of the rotatable member 7, e.g. in the monochromator 1 the scanning of the wavelength range in the order of increasing wavelenth corresponds to the openings 26, while the scanning in the order of decreasing wave length corresponds to the openings 26A. This can be realized e.g. with a monochromator 1 having an oscillating grating.

In course of the measurement the data processing unit 14 controls the number of the rotations of the rotatable member 7 during which the zero level and spectrum data are to be measured and stored. After the required number of measuring periods necessary for the averaging operation to decrease the effect of noise and interferences, the motor 3 is stopped by the data processing unit 14 via the motor control unit 28, and the data containing the stored spectrum and zero level values are processed by the data processing unit 14. In course of this operation the spectrum values are modified by correction values generated by means of the related zero level values, and the spectrum values measured several times at the same wavelength are averaged. The modified spectrum can be graphically displayed by the display unit 15.

In the embodiment of the invention illustrated in FIGS. 1 and 2 the spectrum values measured and stored are modified on the basis of the zero level values also measured and stored in such a manner that, within the period related to the zero level values corresponding to the openings 27 and 29, the zero level values related to the time values corresponding to the openings 26 are determined by linear interpolation and these latter values are subtracted from the measured spectrum values corresponding to the openings 26. E.g. let the time interval between two subsequent zero level measurements corresponding to openings 27 and 29 be T, then the calculated zero level value at any intermediate time value t is $$U_h = U_o + t/T(U_T - U_o) \qquad (1)$$

where $U_o$ and $U_T$ are the measured zero level values corresponding to the openings 27 and 29, and $0 \leq t \leq T$. So the modified spectrum value $U_s'$ related to any one of the openings 26 is the following:

$$U_s' = U_s - U_h(t_s) \qquad (2)$$

where $t_s$ is the time interval elapsed from the time of the previous zero level measurement corresponding to the opening 27 until the time of the spectrum measurement corresponding to any one of the openings 26, and $U_s$ is the stored spectrum value measured at $t_s$. Combining equation(1) and equation(2) we get:

$$U_s' = U_s - U_o - t_s/T(U_T - U_o). \qquad (3)$$

Therefore to modify the stored spectrum values, in addition to the stored zero level values the time data are also required. As the rotational speed of the rotatable member 7 is constant, these data are also constants defined by the position of the openings provided in the rotatable member 7, so these constants can be taken into consideration when programming the data processing unit 14.

In an apparatus corresponding to the present invention the value of the time interval T can be e.g. 50 to 400 ms. In a given case, to attain an acceptable accuracy of the spectrum values, it may be sufficient to measure the zero level signal only after the spectrum signal measurement and to suppose a zero level signal equal to zero at the moment of zeroing. For this embodiment only the openings 27 and 27A should be omitted from the rotatable member 7 as illustrated in FIG. 2. If the time interval T is between the zeroing corresponding to the opening 23 and the measurement of the zero level corresponding to the opening 29, the equation(1) can be written as $$U_h = t/T U_T. \qquad (4)$$

Thus the relation corresponding to equation(3) is $$U_s' = U_s - t_s/T U_T. \qquad (5)$$

Figure 3:
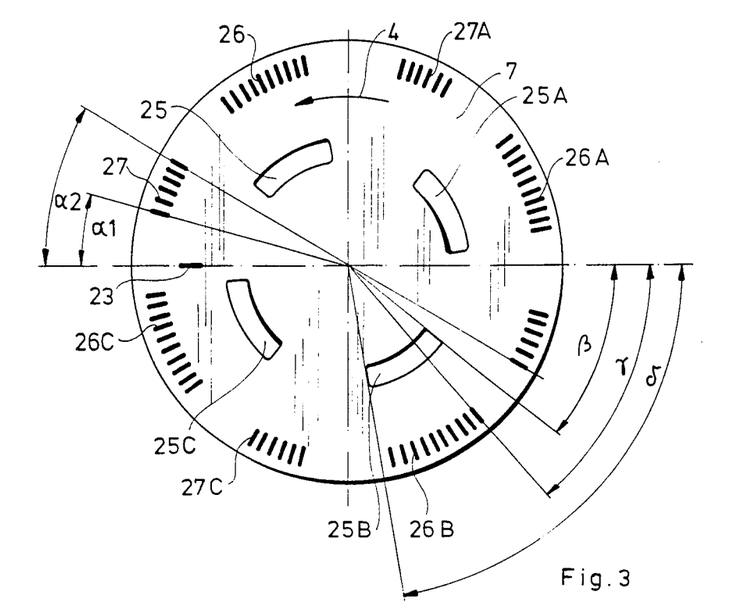
FIG. 3 shows a top view of another possible embodiment of the disc-shaped rotatable member of the apparatus illustrated in FIG. 1.

Another possible embodiment of the rotatable member 7 applied in the apparatus given in FIG. 1 is illustrated in FIG. 3. This rotatable member 7 consists of four symmetrical quarters. Following the zero setting corresponding to the opening 23 six openings 27 are positioned to initiate zero level measurements between angles α1 and α2. Following this, at an angle β, the section 25B transparent to the radiation opens the path of the radiation beam emitted from the monochromator 1, and then ten spectrum signal measurements will be performed corresponding to the openings 26 positioned between angles γ and δ. It can be seen, that the openings 26 are positioned asymmetrically in the range of the section 25 transparent to the radiation, to provide the necessary time delay for the sensor 11 for the transition from dark into exposed condition. After that the rotatable member 7 cuts off again the path of the radiation beam emitted from the monochromator 1 and, when the dark condition of the sensor 11 is settled again, the sequence of measurements described in the first quarter will be repeated again with new zero level measurements corresponding to the openings 27A.

With this embodiment one complete turn of the rotatable member 7 will result the measuring of e.g. four different spectrum signals ten times each, and each series consisting of ten spectrum signal measurements is preceded by a zero level signal measurement, too. Following the series consisting of four measurements a zeroing will follow corresponding to the opening 23, followed by the measurement of the next four spectrum values. In this case the correction values for the measured and stored spectrum values for each complete turn are determined by an interpolation for the spectrum values corresponding to the openings 26, 26A and 26B based on the four zero level values corresponding to the openings 27, 27A, 27B and 27C, each of them obtained by averaging six measured and stored values, and by an extrapolation for the spectrum values corresponding to the openings 26C, respectively. The interpolation is expediently performed by determining a function versus time approximating the zero level values related to each complete turns, and the spectrum values, corresponding to the openings 26, 26A and 26B and obtained by averaging ten values, are to be modified according to this function. In the range following the zero level values corresponding to the openings 27C, the value of the function is determined e.g. by linear extrapolation, and the spectrum values corresponding to the openings 26C and obtained also by averaging ten values are to be modified according to this extrapolated function.

Figure 4:
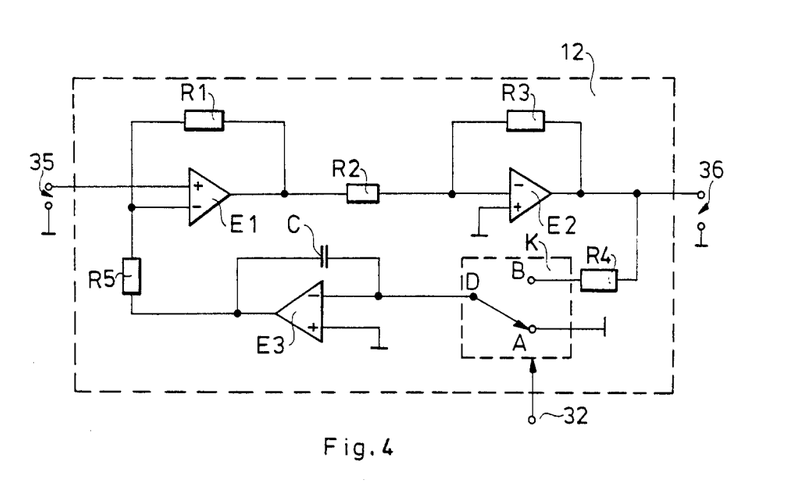
FIG. 4 shows a possible embodiment of the zeroable amplifier of the apparatus illustrated in FIG. 1.

An advantageous embodiment of the zeroable amplifier 12 is illustrated in FIG. 4. The input 35 is connected to the non-inverting input of an operational amplifier E1, the output of said amplifier E1 is connected to its inverting input via a feedback resistor R1. The output of the amplifier E1 is connected to the inverting input of an operational amplifier E2 through a serial resistor R2, and the output of the amplifier E2 is fed back to the same input via a resistor R3. The non-inverting input of the amplifier E2 is connected to the common point of the circuit. The output of the amplifier E2 represents the output 36 of the amplifier 12, and at the same time it is connected to the point B of a change-over switch K via a serial resistor R4. The change-over switch K is controlled from the input 32 and the point A of it is connected to the common point while the point D is connected to the inverting input of an operational amplifier E3. The other input of the amplifier E3 is connected to the common point, and its output is partly fed back to its inverting input via a capacitor C, partly connected to the inverting input of the amplifier E1 via a serial resistor R5.

When the change-over switch K of the amplifier 12 is controlled by a zeroing pulse applied to the input 32 to make a galvanic contact points D and B, the closed control circuit produces zero voltage on the output 36 even if an error voltage differing from zero exists on the input 35. When the zeroing pulse on the input 32 ceases to exist, the switch K makes a galvanic contact between points D and A thereby setting the amplifier 12 in an amplifying mode and the status of being set to zero is retained until the next zeroing as a consequence of the charge stored in the capacitor C. The frequency of the zeroing operation should be suitably selected according to the time constants of the circuit.

Figure 5:
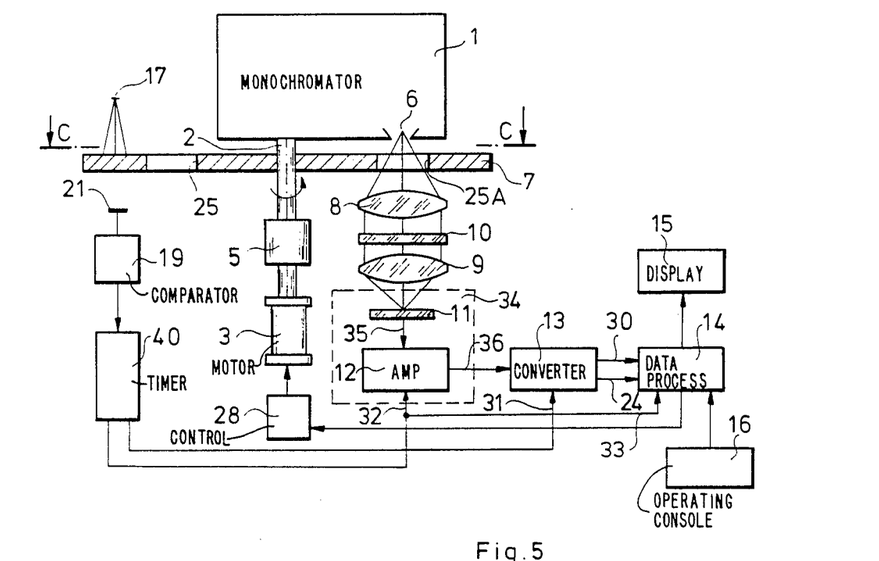
FIG. 5 is the block diagram of another embodiment of the apparatus according to the invention.
Figure 6:
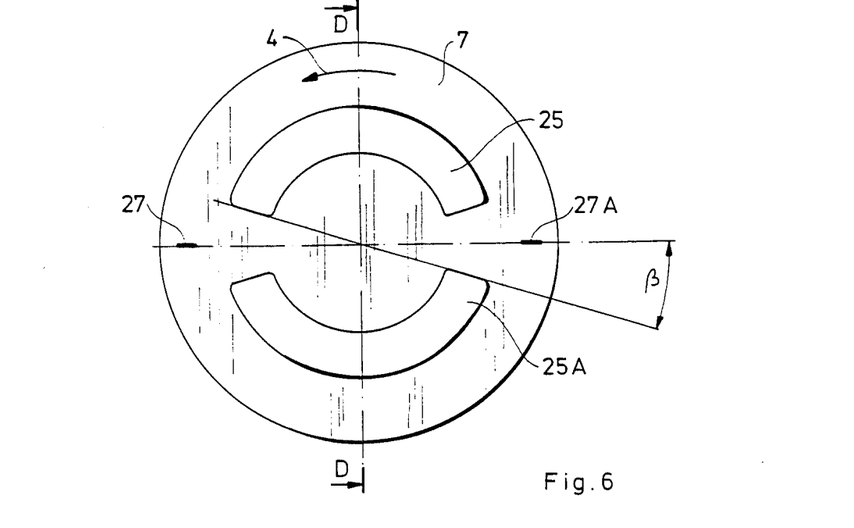
FIG. 6 is a top view of the disc-shaped rotatable member of the apparatus illustrated in FIG. 5.

A further embodiment of the apparatus according to the invention is illustrated in FIGS. 5 and 6, where the elements corresponding to the embodiment illustrated in FIG. 1 are provided with the same reference numbers. The top view of the rotatable member 7 taken along the section line C—C of FIG. 5 is shown in FIG. 6. In FIG. 5 a sectional view of the rotatable member 7 can be seen taken along the section line D—D of FIG. 6. Not as in FIG. 1, in this embodiment there is only one auxiliary light source 17 transmitting a light pulse to the auxiliary detector 21 under the effect of the opening 27 provided in the rotatable member 7, which detector 21 in turn transmits a start pulse to a timing circuit 40 via the comparator 19. As a result of the start pulse, a zeroing pulse will be transmitted from one output of the timing circuit 40 to the zeroing input 32 of the intensity measuring unit 34 and then, after a certain time delay but before the rotatable member 7 is rotated through the angle $\beta$, a pulse will be transmitted from the other output of the timing circuit 40 to the control input 31 of the analog-to-digital converter 13. As a result of this latter, the zero level signal of the intensity measuring unit 34 is measured by the analog-to-digital converter 13. After that, with a delay of time longer than that necessary to rotate the rotatable member 7 through the angle $\beta$, the timing circuit 40 starts to transmit a series of pulses to the input 31 of the analog-to-digital converter 13. These pulses initiate the spectrum signal measurements corresponding to the pulses generated by the openings 26 shown in FIG. 2. Following this series of pulses a properly delayed additional pulse is transmitted by the timing circuit 40 to the input 31 of the analog-to-digital converter 13 corresponding to the opening 29 in FIG. 2. The measuring cycle described above is repeated as a result of the start pulse corresponding to the opening 27A. The timing circuit 40 can be constructed from common digital circuits and delay elements, but it can be realized by a microprocessor, too.

Figure 7:
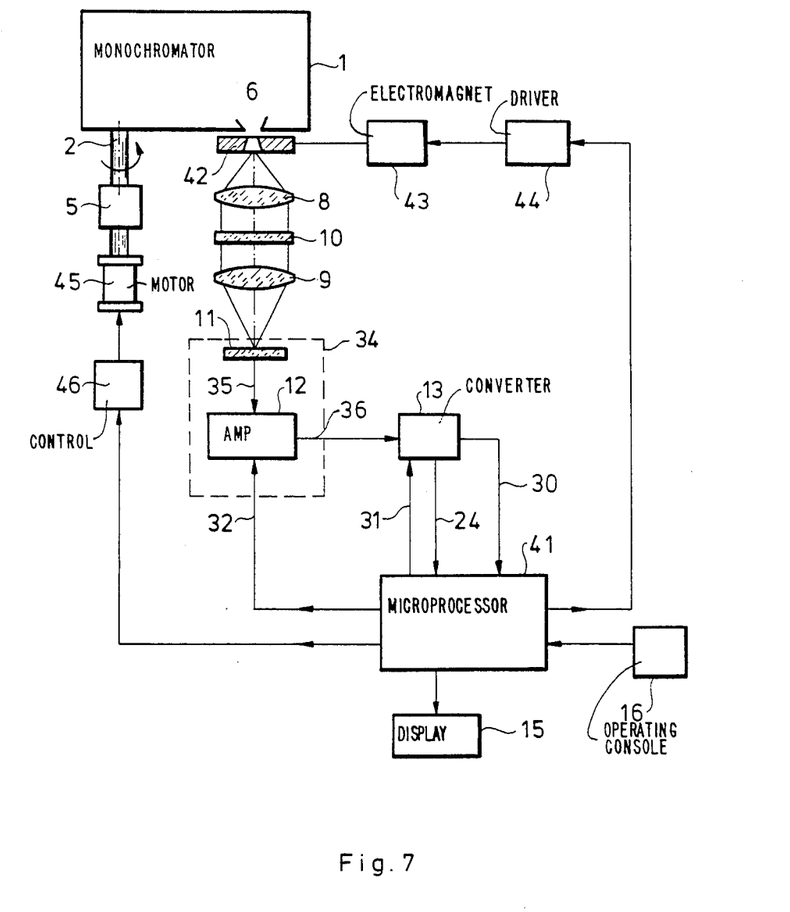
FIG. 7 illustrates the block diagram of a further embodiment of the apparatus according to the invention.

A further embodiment of the apparatus according to the invention is illustrated in FIG. 7, where the elements corresponding to the embodiment illustrated in FIG. 1 are provided with the same reference numbers. In this embodiment the complete apparatus is controlled by a microprocessor 41 with an operating console 16 and a display unit 15 connected to it. On the one hand, the microprocessor 41 controls a stepper motor 45 via a motor control unit 46, which stepper motor 45 drives the shaft 2 controlling the wavelength of the monochromator 1 via the unit 5 changing the speed of rotation. On the other hand, the microprocessor 41 controls an electromagnet 43 via a driver unit 44, which electromagnet 43 operates a diaphragm 42 cutting off and transmitting, respectively, the radiation beam emitted from the exit slit 6 of the monochromator 1. The microprocessor 41 further controls the zeroing of the intensity measuring unit 34 by a signal applied to the input 32, and the operation of the analog-to-digital converter 13 by a signal applied to the input 31. The output digital signals from the digital-to-analog converter 13 will also be transmitted to the microprocessor 41 via the line 30, and these digital signals will be stored in the memory of the microprocessor 41.

The measuring process is started by a start signal received from the operating console 16 and is completely controlled by the microprocessor 41. After storing the required zero level signal and spectrum values, the microprocessor 41 generates the function approximating the variations of the zero level signal by means of interpolation or interpolation and extrapolation based on the stored zero level values, calculates the correction values given by this function, and subtracts the correction values from the stored spectrum values. If necessary, the microprocessor 41 performs the averaging of the stored spectrum values and zero level values, respectively, before performing the arithmetic operations described above, in order to decrease the effect of noise and interferences always existing in measurements. The microprocessor 41 itself can be realized from widely known commercial circuit elements.

The embodiments described above are examples only, the method and apparatus according to the invention can be realized in different ways, too. e.g. in case of a very high stability of the intensity measuring unit 34, only one zeroing operation may be sufficient prior to a spectrum measurement or several spectrum measurements and thereby the cyclic zeroing related to the openings 23 in FIGS. 2 and 3 and corresponding to FIGS. 5 and 7, respectively, may be omitted. Although transmission spectrum measurement is generally illustrated in the Figures, it is to be recognized that the invention is applicable for reflection spectrum measurements, or in the case of luminescent substances for conversion spectrum measurements, too. As to the invention, the construction of the monochromator applied is not specific, any type with proper control of the wave length is applicable. Switching on and off the radiation beam may also be effected under purely electronic control, e.g. when the monochromator is a tunable laser light source. In the apparatus according to the invention it may be advantageous to utilize an integrating type analog-to-digital converter 13. In this particular case e.g. in the embodiment illustrated in FIGS. 1 and 3 both the six measurements corresponding to the openings 27 and the ten measurements corresponding to the openings 26 may be replace by one measurement each, and at the same time the proper rejection of the noise and interferences is also effected. Thereby the averaging operation to be performed in the course of the data processing may be replaced by an analog integration resulting in a significant reduction of the memory requirement of the data processing unit and in the reduction of the time necessary for the data processing.

We claim:

1. A method for measuring the spectrum of a material comprising the steps of
   irradiating a sample of the material to be tested successively by radiations of different wavelengths of the spectrum to be measured;
   measuring and storing spectrum signals produced by an intensity measuring unit in response to the radiation reflected or transmitted by the sample irradiated;
   measuring and storing zero level signals produced by the intensity measuring unit in the unradiated condition of the sample at least two times in the course of said spectrum signal measurements;
   calculating correction values for the stored spectrum values by interpolation based on the stored zero level values; and
   subtracting from the stored spectrum values the respective calculated correction values to produce corrected spectrum values.

2. The method according to claim 1, wherein said interpolation is linear.

3. The method according to claim 1, wherein said measuring and storing of the zero level signals are performed a plurality of times in the course of said spectrum signal measurements, and said interpolation is based on a function versus time approximating the stored zero level values.

4. The method according to claim 1, wherein said measuring and storing of the zero level signals are performed before and after said spectrum signal measurements at different wavelengths.

5. The method according to claim 1, wherein said measuring and storing of the spectrum signals are performed in successive groups by measuring and storing spectrum signals of substantially the same wavelength in each group a plurality of times; and said measuring and storing of the zero level signals are performed before or after each group a plurality of times.

6. The method according to claim 5, wherein the measured spectrum signals in each group are averaged; and the zero level signals measured before or after each group are also averaged.

7. The according to claim 5, wherein said intensity measuring unit is set to zero in the unradiated condition of the sample before the first group; said measuring and storing of the zero level signals are performed after each group a plurality of times; and in calculating the correction values a zero value of the zero level signal at the time of said setting to zero is also taken into account.

8. A method for measuring the spectrum of a material comprising the steps of
   irradiating a sample of the material to be tested successively by radiations of different wavelengths of the spectrum to be measured;
   measuring and storing spectrum signals produced by an intensity measuring unit in response to the radiation reflected or transmitted by the sample irradiated;
   measuring and storing zero level signals produced by the intensity measuring unit in the unradiated condition of the sample at least two times in the course of said spectrum signal measurements;
   calculating correction values for the stored spectrum values measured before the measurement of the last zero level value by interpolation based on the stored zero level values;
   calcualating correction values for the stored spectrum values measured after the measurement of the last zero level value by extrapolation based on the stored zero level values; and
   substracting from the stored spectrum values the respective calcualted correction values to produce corrected spectrum values.

9. The method according to claim 8, wherein said interpolation and extrapolation are linear.

10. The method according to claim 8, wherein said measuring and storing of the zero level signals are performed a plurality of times in the course of said spectrum signal measurements, and said interpolation and extrapolation are based on a function versus time approximating the stored zero level values.

11. The method according to claim 8, wherein said measuring and storing of the spectrum signals are performed in successive groups by measuring and storing spectrum signals of substantially the same wavelength in each group a plurality of times; and said measuring and storing of the zero level signals are performed before each group a plurality of times.

12. The method according to claim 11, wherein the measured spectrum signals in each group are averaged; and the zero level signals measured before or after each group are also averaged.

13. The method according to claim 11, wherein said intensity measuring unit is set to zero in the unradiated condition of the sample before the first measuring and storing of the zero level signal.

* * * * *